(12) United States Patent
Mitchell, II

(10) Patent No.: US 9,255,249 B2
(45) Date of Patent: Feb. 9, 2016

(54) ISOLATION AND PURIFICATION OF HEMATOPOIETIC STEM CELLS FROM POST-LIPOSUCTION LIPOASPIRATES

(75) Inventor: James B. Mitchell, II, Abingdon, MD (US)

(73) Assignee: Cognate BioServices, Inc., Baltimore, MD (US)

( * ) Notice: Subject to any disclaimer, the term of this patent is extended or adjusted under 35 U.S.C. 154(b) by 1028 days.

(21) Appl. No.: 11/650,723

(22) Filed: Jan. 8, 2007

(65) Prior Publication Data
US 2007/0274965 A1    Nov. 29, 2007

Related U.S. Application Data

(60) Provisional application No. 60/801,120, filed on May 17, 2006.

(51) Int. Cl.
*C12N 5/00*     (2006.01)
*C12N 5/0789*   (2010.01)

(52) U.S. Cl.
CPC .................................. *C12N 5/0647* (2013.01)

(58) Field of Classification Search
CPC ............... C12N 5/0647; C12N 2502/1388; C12N 5/0653; A61K 2300/00; A61K 35/12; A61K 35/28
See application file for complete search history.

(56) References Cited

U.S. PATENT DOCUMENTS

| | | | |
|---|---|---|---|
| 5,154,921 A * | 10/1992 | Sager et al. ................... | 424/93.7 |
| 5,981,708 A | 11/1999 | Lawman et al. .............. | 530/351 |
| 6,555,374 B1 | 4/2003 | Gimble et al. ................. | 435/371 |
| 6,627,759 B1 * | 9/2003 | Smith et al. ................... | 548/405 |
| 6,878,371 B2 * | 4/2005 | Ueno et al. .................... | 424/93.1 |
| 7,078,230 B2 * | 7/2006 | Wilkison et al. .............. | 435/325 |
| 2001/0033834 A1 | 10/2001 | Wilkison et al. | |
| 2004/0028661 A1* | 2/2004 | Bartelmez ................. | 424/93.21 |
| 2004/0067218 A1 | 4/2004 | Casteilla et al. | |
| 2005/0048034 A1* | 3/2005 | Fraser et al. ................. | 424/93.7 |

FOREIGN PATENT DOCUMENTS

| | | |
|---|---|---|
| JP | 9-322757 A | 12/1997 |
| JP | H10-84950 A | 4/1998 |
| JP | 2006-067858 A | 3/2006 |
| WO | WO 95/19793 A1 | 7/1995 |
| WO | WO 98/28406 A1 | 7/1998 |
| WO | WO 99/15684 A3 | 4/1999 |
| WO | WO 02/44343 A2 | 6/2002 |
| WO | WO 02/055678 | 7/2002 |
| WO | WO 02/083120 A2 | 10/2002 |
| WO | WO 2005/046596 A2 | 5/2005 |
| WO | WO 2005/083061 A1 | 9/2005 |

OTHER PUBLICATIONS

Zhou S et al, The ABC transporter Bcrp1/ABCG2 is expressed in a wide variety of stem cells and is a molecular determinant of the side-population phenotype, 7 Nature Medicine 1028-34 (2001).*

Gronthos S et al. 2001. Surface Protein Characterization of Human Adipose Tissue-Derived Stromal Cells. J Cell Physiol 189: 54-63.*

Berenson et al., 1991, "Engraftment After Infusion of CD34 Marrow Cells in Patients With Breast Cancer or Neuroblastoma", Blood 77:1717-1722.

Bjornson, 1999, "Turning Brain into Blood: A Hematopoietic Fate Adopted by Adult Neural Stem Cells in Vivo", Science 283:534-537.

Cousin et al., 2003, "Reconstitution of lethally irradiated mice by cells isolated from adipose tissue", Biochem. Biophys. Res. Commun. 301:1016-1022.

Fallon et al., 2003, "Mobilized peripheral blood SSCloALDHbr cells have the phenotypic and functional properties of primitive haematopoietic cells and their number correlates with engraftment following autologous transplantation" Br. J. Haematol. 122:99-108.

Hess et al., 2004, "Functional characterization of highly purified human hematopoietic repopulating cells isolated according to aldehyde dehydrogenase activity", Blood 104:1648-1655.

Jackson et al., 1999, "Hematopoietic potential of stem cells isolated from murine skeletal muscle", PNAS 96:14482-14486.

Kim et al., 2005, "Human adipose stromal cells expanded in human serum promote engraftment of human peripheral blood hematopoietic stem cells in NOD/SCID mice", Biochem. Biophys. Res. Commun. 329(1):25-31.

McIntosh et al., 2006, "The immunogenicity of human adiopose derived cells: Temporal changes in vitro", Stem Cells 24(5):1246-53 (Epub Jan. 12, 2006).

Mitchell et al., 2006, "Immunophenotype of Human Adipose-Derived Cells: Temporal Changes in Stromal-Associated and Stem Cell-Associated Markers", Stem Cells 24(2):376-85 (Epub Dec. 1, 2005).

Quesenberry et al., 1999, "Correlates between Hematopoiesis and Neuropoiesis: Neural Stem Cells" J. Neurotrauma 16:661-666.

Scheffler et al., 1999, "Marrow-mindedness: a perspective on neuropoiesis", Trends Neurosci 22:348-357.

Storms et al., 1999, "Isolation of primitive human hematopoietic progenitors on the basis of aldehyde dehydrogenase activity", Proc. Natl. Acad. Sci. 96:9118-9123.

Svendsen & Smith, 1999, "New prospects for human stem-cell therapy in the nervous system", Trends Neurosci 22:357-364.

Wang et al., 1997, "Primitive Human Hematopoietic Cells Are Enriched in Cord Blood Compared With Adult Bone Marrow or Mobilized Peripheral Blood as Measured by the Quantitative In Vivo SCID-Repopulating Cell Assay", Blood 89:3919-3924.

Storms et al., "Distinct hematopoietic progenitor compartments are delineated by the expression of aldehyde dehydrogenase and CD34," *Blood* 106(1):95-102, 2005.

Kazuhiro Sudo et al.: "*Age-associated Characteristics of Murine Hematopoietic Stem Cells*"; J. Exp. Med., vol. 192, No. 9, Nov. 6, 2000, pp. 1273-1280.

(Continued)

*Primary Examiner* — Lora E Barnhart Driscoll
(74) *Attorney, Agent, or Firm* — DLA Piper LLP (US)

(57) ABSTRACT

The present invention relates to a method of isolating hematopoietic stem cells from adipose tissue. The method yields a notably high number of $CD34^+$, $ALDH^{br}$ and/or $ABCG2$-expressing cells, comprising hematopoietic stem cells, permitting the use of the cells with no or minimal expansion.

8 Claims, 8 Drawing Sheets

(56) References Cited

OTHER PUBLICATIONS

Dong Ku Kim et al.: "*Comparison of Hematopoietic Activities of Human Bone Marrow and Umbilical Cord Blood CD34 Positive and Negative Cells*"; Stem Cells, 1999; vol. 17, pp. 286-294.

Corey Cutler et al.: "*Peripheral Blood Stem Cells for Allogeneic Transplantation: A Review*"; Stem Cells, 2001; vol. 19, pp. 108-117.

J. Chen et al.: "*Development and aging of primitive hematopoietic stem cells in BALB/cBy mice*"; Experimental Hematology, May 1999, vol. 27(5), 2 pages.

Mitchell J B et al: "*Immunophenotype of Human Adipose-Derived Cells: Temporal Changes in Stromal-Associated and Stem Cell-Associated Markers*"; Stem Cells, Alphamed Press, Dayton, OH, US, vol. 24, No. 2, Feb. 1, 2006, pp. 376-385, XP009068575, ISSN: 1066-5099.

Jansen Jan et al: "*Transplantation of hematopoietic stem cells from the peripheral blood*", Journal of Cellular and Molecular Medicine, vol. 9, No. 1, Jan. 2005, pp. 37-50, XP002714332, ISSN: 1582-1838.

Mlikhopadhyay Asok et al: "*Hematopoietic stem cells: clinical requirements and developments in ex-vivo culture.*", Advances in Biochemical Engineering/Biotechnology 2004, vol. 86, pp. 215-253, XP002714333, ISSN: 0724-6145.

\* cited by examiner

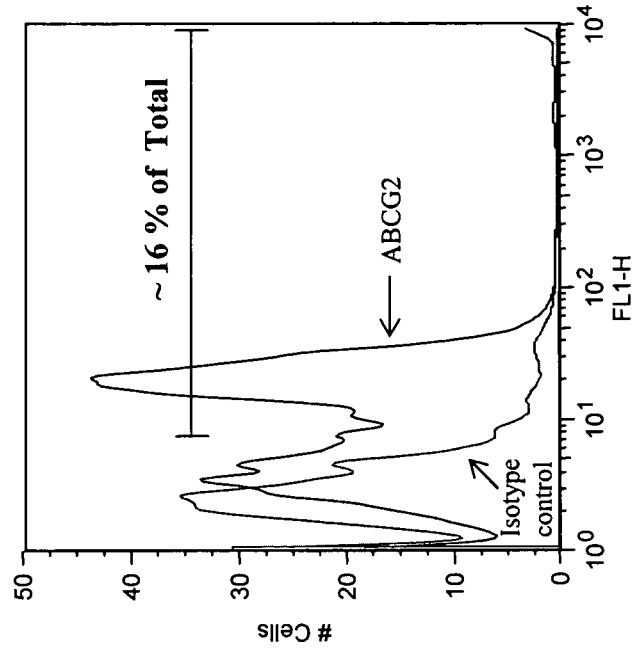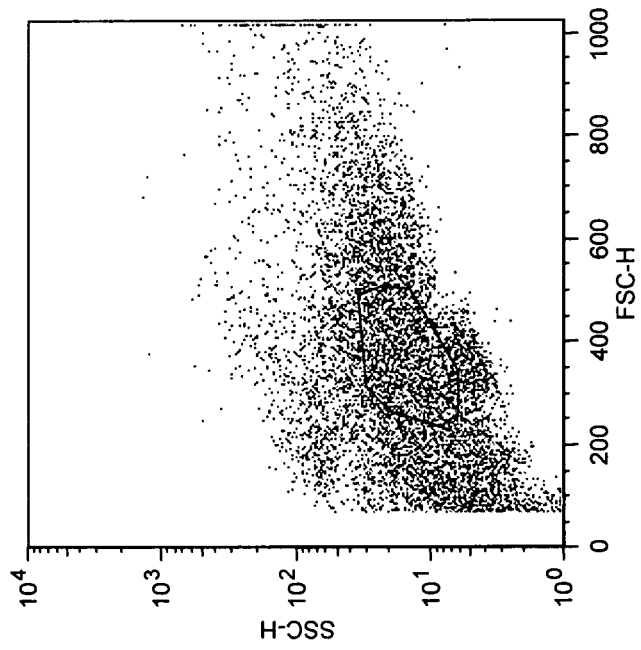

ISOLATION AND PURIFICATION OF HEMATOPOIETIC STEM CELLS FROM POST-LIPOSUCTION LIPOASPIRATES

CROSS-REFERENCE TO RELATED APPLICATIONS

This application claims the benefit pursuant to 35 U.S.C. §119(e) of U.S. Provisional Application No. 60/801,120, filed May 17, 2006, which is hereby incorporated by reference in its entirety herein.

BACKGROUND OF THE INVENTION

Hematopoietic stem cells (HSCs) are stem cells that form blood and immune cells and are ultimately responsible for the constant renewal of blood in an organism throughout the lifetime of the organism. HSCs have been the focus of research for many decades and are now routinely used for many therapeutic applications, including treatment for leukemia, lymphoma, inherited blood disorders, and HSC rescue after extensive chemotherapy regimens, among others.

HSCs are the best characterized example of a multipotential stem cell existing in tissues of an adult organism. In seminal studies by Trentin and colleagues (Trentin, 1965, Cardiovasc. Res. Cent. Bull 4:38-4; Till & McCulloch, 1961, Rad. Res. 14:213-222) lethally-irradiated mice died because they failed to replenish their circulating blood cells. However, transplantation of bone marrow cells from syngeneic donor animals rescued the host animal. The donor cells were responsible for repopulating all of the circulating blood cells. More recently, it has been shown that the cells responsible for reconstituting hematopoiesis in humans receiving a bone marrow transplant reside in a subset of cells expressing the CD34 antigen (CD34$^+$) (Berenson et al., 1991, Blood 77:1717-1722). In other words, CD34$^+$ cells comprise hematopoietic stem cells. Other methods of identifying and isolating populations enriched for hematopoietic stem cells that do not rely on cell surface immunophenotypes have been pursued. Primitive human hematopoietic progenitors have been isolated based on aldehyde dehydrogenase (ALDH) activity (Storms et al., 1999, Proc. Natl. Acad. Sci. 96:9118-9123; Hess et al., 2004, Blood 104:1648-1655)). In addition, engraftment in humans is highly correlated with the number of cells infused having ALDH activity (ALDH$^{br}$) and low side scatter (SSC$^{lo}$) (Fallon et al., 2003, Br. J. Haematol. 122:99-108).

A wealth of elegant studies have demonstrated that donation of a finite number of undifferentiated hematopoietic stem cells is capable of regenerating each of the eight or more different blood cell lineages in a host animal. This large body of work has provided the basis for bone marrow transplantation, a widely accepted therapeutic modality for cancer and inborn errors of metabolism. Thus, hematopoietic stem cells remain present in normal human bone marrow throughout life; they are not limited to the neonatal period.

There are currently three major sources of hematopoietic stem cells (HSCs) used for the purpose of bone marrow transplantation: adult bone marrow, adult peripheral blood, and the mononuclear fraction of umbilical cord blood following child birth. Cells isolated for the purpose of transplantation are typically isolated from the bone marrow or peripheral blood of adults. Disadvantageously, however, CD34$^+$ cells are extremely rare in adult bone marrow (~1-2%), requiring a significant volume of marrow to be obtained to generate a sufficient quantity of HSCs to engraft an adult. The procedure to obtain bone marrow is a lengthy and unpleasant procedure for the marrow donor, requiring extended hospitalizations to allow for bone marrow recovery. Isolation of CD34$^+$ or ALDH$^{br}$ cells from peripheral blood, typically requiring multiple cytapheresis sessions, is less unpleasant for the donor, however, it requires pre-inoculation of the donor with cytokines to mobilize the HSCs to the peripheral blood. Despite the mobilization, the number of CD34$^+$ or ALDH$^{br}$ cells, and consequently, HSCs, in peripheral blood is still typically quite low.

Umbilical cord blood (UCB) is somewhat more enriched for CD34$^+$ cells, compared to bone marrow or mobilized peripheral blood (Wang et al., 1997, Blood 89:3919-3924), but the small volume of blood available in an umbilical cord limits the absolute number of engraftable HSCs that can be recovered, making UCB less useful than originally anticipated. In theory, one could provide a sufficient number of HSCs by pooling multiple umbilical cord blood samples, however, pooling is frowned on in clinical practice. Thus, cord blood-derived CD34$^+$ cells are limited in their utility in adults because the consequential low numbers of HSCs isolated are too few to successfully engraft a full-grown adult. Expansion protocols have been studied to try and increase the cell numbers. Typically, however HSC expansion is accompanied by substantial differentiation, which is not always desirable.

There is a growing body of evidence that hematopoietic progenitors may not be limited to the bone marrow microenvironment. Investigators at University of Calgary have examined neuronal stem cells, which routinely differentiate along neuronal cell lineage pathways. When these cells were transplanted into lethally-irradiated hosts, the investigators detected the presence of donor cell markers in newly-produced myeloid and lymphoid cells (Bjornson, 1999, Science 283:534-537). Investigators at Baylor College of Medicine have performed similar studies using satellite cells isolated from murine skeletal muscle (Jackson et al., 1999, PNAS 96:14482-14486). When these muscle-derived cells were transplanted into lethally-irradiated hosts, the investigators detected the presence of the muscle gene markers in all blood cell lineages. Together, these studies indicate that neuronal and muscle tissues contain stem cells capable of hematopoietic differentiation. This suggests that sites other than the bone marrow may provide a renewable source of hematopoietic progenitors with potential application to human disease therapy (Quesenberry et al., 1999, J. Neurotrauma 16:661-666: Scheffler et al., 1999, Trends Neurosci 22:348-357; Svendsen & Smith, 1999, Trends Neurosci 22:357-364).

More recently, adipose-derived stromal vascular fraction (SVF) cells have been shown to successfully reconstitute major hematopoietic lineages in lethally-irradiated mice (Cousin et al., 2003, Biochem. Biophys. Res. Commun. 301: 1016-1022 and U.S. Patent Publication No. 2004/0067218). Mesenchymal stromal stem cells, isolated from adipose tissue, have also been co-infused with CD34$^+$ cells, isolated from mobilized peripheral blood, and were found to facilitate successful engraftment of the CD34$^+$ cells (Kim et al., 2005, Biochem. Biophys. Res. Commun. 329(1):25-31).

U.S. Patent Publication No. 2001/0033834 discloses an isolated adipose-derived stromal cell that has been differentiated to express at least one characteristic of a hematopoietic progenitor cell. Also disclosed are adipose-derived stromal cells that are de-differentiated into fully functional pleuripotent stem cells that can then be differentiated into hematopoietic cell lineages.

Despite the work summarized above, there remains a need for an abundant source of hematopoietic stem cells for use in therapeutic and other applications. The present invention addresses and meets these needs.

BRIEF SUMMARY OF THE INVENTION

The present invention encompasses a method for isolating a hematopoietic stem cell from adipose tissue, the method comprising the steps of obtaining adipose tissue; preparing a stromal vascular fraction (SVF) from the adipose tissue; and isolating nonadherent cells in the SVF, wherein the nonadherent cells comprise a hematopoietic stem cell. Preferably, the adipose tissue is human. In one embodiment, the adipose tissue is obtained from lipoaspirates.

In one embodiment, the hematopoietic stem cell is selected from the group consisting of a $ALDH^{br}SSC^{lo}$ cell, a $CD34^+$ cell, a $CD34^+SSC^{lo}$ cell, a $CD34^+CD45^+$ cell, a $CD34^+CD38^-CD41^-$ cell, a $CD34^+CD45^-$ cell, a $CD34^+CD38^-CD41^-SSC^{lo}$ cell, and a ABCG2-expressing cell. In another embodiment, the hematopoietic stem cell is selected from the group consisting a colony-forming unit granulocyte macrophage (CFU-GM), a burst-forming unit erythrocyte (BFU-E) and a colony-forming unit granulocyte erythrocyte macrophage megakaryocyte (CFU-GEMM).

In another embodiment, the method for isolating a hematopoietic stem cell further comprises isolating a $CD34^{hi}$ cell from the nonadherent cells. In another embodiment, the method further comprises isolating an $ALDH^{br}$ cell from the nonadherent cells. In one aspect, the $ALDH^{br}$ cell is $ALDH^{br}SSC^{lo}$.

The invention also provides a method for isolating a $CD34^+$ cell, the method comprising the steps of obtaining adipose tissue; preparing a stromal vascular fraction (SVF) from the adipose tissue; separating nonadherent cells in the SVF from the adherent cells, and isolating a $CD34^+$ cell from the nonadherent cells, thereby isolating a $CD34^+$ cell. Preferably, the adipose tissue is human. A composition comprising $CD34^+$ cells isolated according to the method is provided by the invention, wherein the $CD34^+$ cells are isolated in a ratio of at least about $1 \times 10^5$ $CD34^+$ cells isolated per about 1 milliliter of adipose tissue.

In one embodiment, the adipose tissue is obtained from lipoaspirates. In one embodiment, the SVF comprises at least about 40% $CD34^+$ cells. In one aspect, the $CD34^+$ cell is isolated in the ratio of at least about $1 \times 10^7$ $CD34^+$ cells isolated per about 100 ml of adipose tissue.

In another embodiment, the $CD34^+$ cell is selected from the group consisting of a $CD34^+SSC^{lo}$ cell, a $CD34^+CD45^+$ cell, a $CD34^-CD41^-$ cell, a $CD34^+CD38^-CD41^-SSC^{lo}$, a $CD34^{lo}CD45^-$ cell, a $CD34^{lo}CD45^+$ cell, a $CD34^+ALDH^{br}$ cell and a $CD34^+ALDH^{br}SSC^{lo}$ cell.

In one embodiment, the method for isolating a a $CD34^+$ cell further comprises isolating a $CD34^{hi}$ cell or a $CD34^{lo}$ cell.

A method of providing hematopoietic stem cells to a subject is also provided by the invention. The method comprises the steps of obtaining adipose tissue from a donor subject; preparing a stromal vascular fraction (SVF) from the adipose tissue; isolating nonadherent cells in the SVF; isolating hematopoietic stem cells from the nonadherent cells; and administering a therapeutically effective amount of the hematopoietic stem cells to a recipient subject in need thereof. Preferably, the donor subject and the recipient subject are human. In one embodiment, the donor subject and the recipient subject are the same human. In another embodiment, the donor subject and the recipient subject are not the same human.

In one embodiment of the method of providing hematopoietic stem cells, the hematopoietic stem cells are $CD34^+$ and are isolated in the ratio of at least about $1 \times 10^7$ $CD34^+$ cells isolated per about 100 ml of adipose tissue.

In one embodiment of the method, the obtaining step comprises lipoaspiration. In another embodiment, the isolating step comprises isolating $ALDH^{br}SSC^{lo}$ cells or $CD34^+CD38^-CD41^-SSC^{lo}$ cells.

A composition of isolated cells comprising at least about 40% nonadherent, stromal vascular fraction (SVF) $CD34^+$ cells is provided by the invention. In one embodiment, the isolated cells comprise at least about 20% $CD34^+$ $CD45^-$ cells. In another embodiment, the stromal vascular fraction is obtained from human adipose tissue. In one embodiment, the $CD34^+$ cells comprise $CD34^+CD38^-CD41^-ALDH^{br}$ cells. In another embodiment, the $CD34^+$ cells comprise $CD34^+CD38^-CD41^-SSC^{lo}$ cells. In yet another embodiment, the $CD34^+$ cells comprise colony-forming unit granulocyte macrophages (CFU-GM), burst-forming unit erythrocytes (BFU-E) and colony-forming unit granulocyte erythrocyte macrophage megakaryocytes (CFU-GEMM). In another embodiment, the cells are genetically modified.

Also provided is a composition of isolated cells comprising at least about 10% nonadherent, stromal vascular fraction (SVF) $ALDH^{br}$ cells. In one embodiment, the composition comprises at least about 15% nonadherent SVF $ALDH^{br}$ cells. In one embodiment, the $ALDH^{br}$ cells are $ALDH^{br}SSC^{lo}$ cells. Preferably, the SVF is obtained from human adipose tissue.

Pharmaceutical compositions comprising one of the compositions of the invention and a pharmaceutically acceptable carrier are also provided.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 8, comprising FIGS. 8A and 8B, is a series of two images depicting ABCG2 expression in nonadherent SVF cells. FIG. 8A is a plot of light scatter properties of nonadherent SVF cells. ABCG2-expressing cells in nonadherent SVF cells are generally found in a discrete region (the circled portion). FIG. 8B is a graph of ABCG2 expression data for nonadherent SVF cells. These data illustrate that about 16% of the nonadherent SVF cells are ABCG2 expressing.

DETAILED DESCRIPTION OF THE INVENTION

Figure 1:
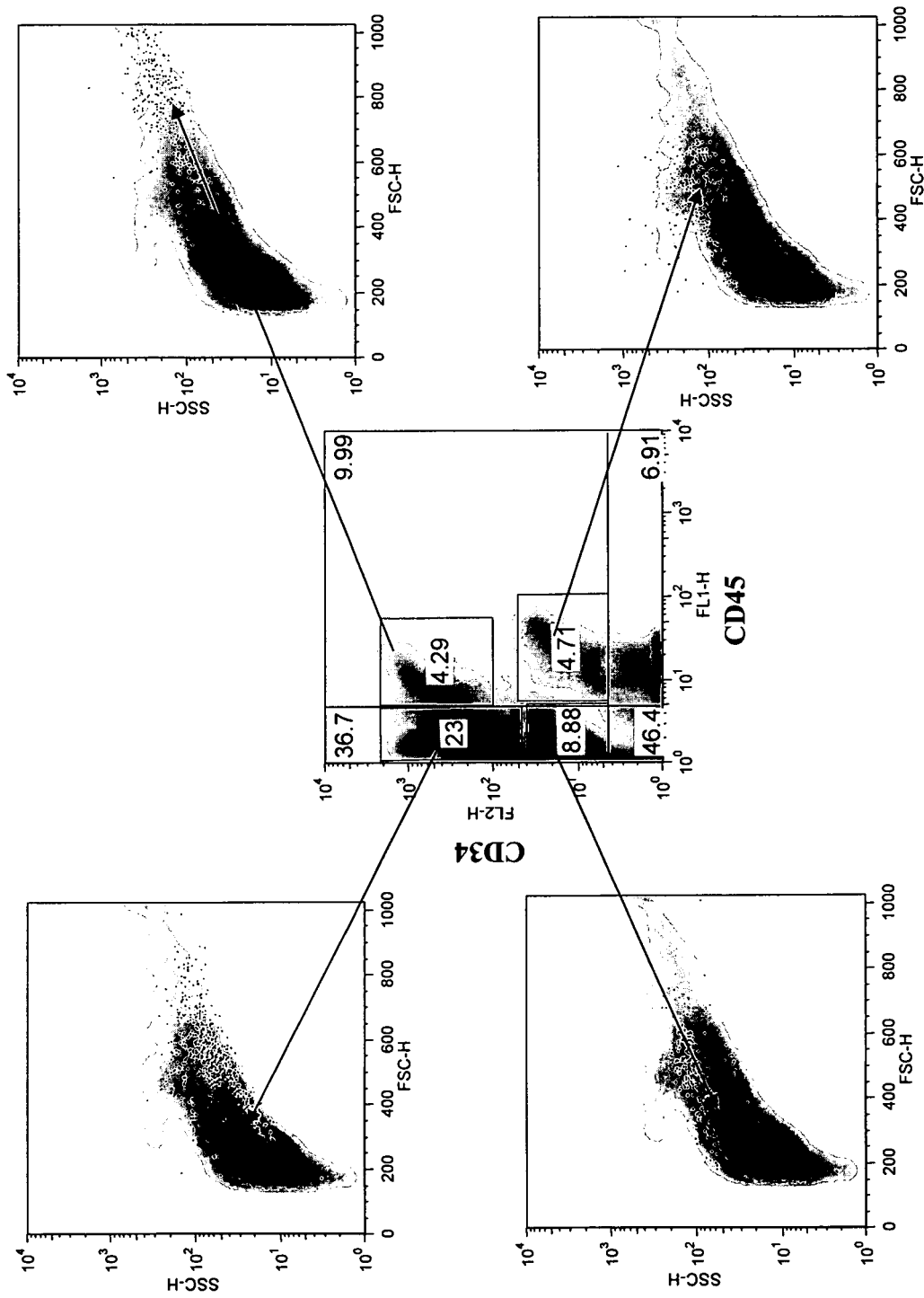
FIG. 1 is a series of plots of flow cytometry light scatter data for various subpopulations of $CD34^+$ cells isolated from adipose tissue nonadherent stromal vascular fraction (SVF). Numbers in the four boxed subpopulations in the center panel represent the percentage of total cells which that subpopulation represents. In the two left and two right panels, the gated population is plotted as black dots and the ungated population is plotted as gray density. SSC-H=side scatter; FSC-H=forward scatter.

The present invention is based, in part, on the observation that nonadherent cells in the stromal vascular fraction (SVF) of adipose tissue are enriched for CD34+ cells, $ALDH^{br}$ cells, $ALDH^{br}SSC^{lo}$ cells and ABCG2-expressing cells, critical markers for HSC identification. Furthermore, it is shown that these cells comprise multipotential hematopoietic progenitors as well as lineage-committed hematopoietic progenitors. The present invention thus provides a method of isolating hematopoietic stem cells from adipose tissue.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y., and Ausubel et al., 2002, Current Protocols in Molecular Biology, John Wiley & Sons, New York, N.Y.), which are provided throughout this document.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

As used herein, "in vitro" and "ex vivo" are used interchangeably to refer to conditions outside the body of a living organism. Thus, in vitro culturing and ex vivo culturing both refer to culturing outside the body of a living organism.

"Adipose" refers to any fat tissue. The adipose tissue may be brown, yellow or white adipose tissue. Adipose tissue includes adipocytes and stroma. Adipose tissue is found throughout the body of an animal. For example, in mammals, adipose tissue is present in the omentum, bone marrow, subcutaneous space, fat pads (e.g., scapular or infrapatellar fat pads), and surrounding most organs. The adipose tissue may be from any organism having fat tissue. A convenient and abundant source of human adipose tissue is that derived from liposuction surgery. However, the source of adipose tissue or the method of isolation of adipose tissue are not critical to the invention.

The term "adipose tissue-derived cell" refers to a cell that originates from adipose tissue. Cells obtained from adipose tissue may be a primary cell culture, a passaged culture, or an immortalized cell line. The initial cell population isolated from adipose tissue is a heterogeneous cell population including, but not limited to, stromal vascular fraction (SVF) cells.

As used herein, the term "adipose derived stromal cells," "adipose tissue-derived stromal cells," "adipose tissue-derived adult stromal (ADAS) cells," or "adipose-derived stem cells" (ASCs) are used interchangeably and refer to stromal cells that originate from adipose tissue which can serve as stem cell-like precursors to a variety of different cell types such as, but not limited to, adipocytes, osteocytes, chondrocytes, muscle and neuronal/glial cell lineages. ASCs are a subset population derived from adipose tissue which can be separated from other components of the adipose tissue using standard culturing procedures known in the art. In addition, ASCs may be isolated from a mixture of cells based on the cell surface markers known in the art.

As used herein, the term "adipose-derived hematopoietic stem cells" refers to nonadherent cells present in the stromal vascular fraction of adipose tissue that comprise one or more HSC characteristics selected from the group consisting of: $CD34^+$, $ALDH^{br}$, $SSC^{lo}$, ABCG2 expression and multipotential hematopoietic progenitor capacity.

As used herein, "nonadherent cells" refer to cells that do not adhere to a tissue culture flask under standard tissue culture conditions for SVF cells. The skilled artisan is familiar with standard tissue culture conditions for SVF cells.

As used herein, "$ALDH^{br}$" refers to bright intracellular fluorescence of a cell expressing a high level of ALDH after administration to the cell of an ALDH substrate that yields a fluorescent product. Detecting $ALDH^{br}$ cells is well known in the art. In addition, the ALDEFLUOR® kit (StemCell Technologies, Vancouver, BC, Canada), used in the identification of ALDH-expressing cells, is commercially available. See also U.S. Pat. No. 5,876,956.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells, which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, the term "multipotential" or "multipotentiality" is meant to refer to the capability of a stem cell to differentiate into more than one type of cell.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, "autologous" refers to a biological material derived from the same individual into whom the material will later be re-introduced.

As used herein, "allogeneic" refers to a biological material derived from a genetically-different individual of the same species as the individual into whom the material will be introduced.

As used herein, "syngeneic" refers to biological material derived from a genetically-identical individual (e.g. identical twin) as the individual into whom the material will be introduced.

As used herein, to "alleviate" a disease, defect, disorder or condition means reducing the severity of one or more symptoms of the disease, defect, disorder or condition.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered. For instance, with regard to the administration of cells to an individual, "therapeutically effective amount" is the amount of cells which is sufficient to provide a beneficial effect to the subject to which the cells are administered.

A "therapeutic" treatment is a treatment administered to a subject who exhibits at least one symptom of pathology for the purpose of treating or alleviating the at least one symptom.

As used herein, the term "growth medium" is meant to refer to a culture medium that promotes proliferation of cells. A growth medium will generally contain animal serum. In some instances, the growth medium may not contain animal serum.

"Differentiation medium" is used herein to refer to a growth medium comprising an additive or a lack of an additive such that a stem cell, HSC, CD34$^+$ cell, adipose-derived adult stem cell or other such progenitor cell, that is not fully differentiated when incubated in the medium, develops into a cell with some or all of the characteristics of a differentiated cell.

As used herein, a "growth factor" is a substance that stimulates proliferation, division and/or maturation of cells. Non-limiting examples of growth factors useful in the instant invention include erythropoietin (EPO), macrophage colony stimulating factor, thrombopoietin (TPO), growth hormone (GH), interleukin 1-α and 1-β, interleukin 3 (IL-3), interleukin 4 (IL-4), interleukin 5 (IL-5), interleukin 6 (IL-6), interleukin 7 (IL-7), interleukin 9 (IL-9), interleukin 10 (IL-10), interleukin 11 (IL-11), interleukin 13 (IL-13), c-kit ligand/stem cell factor (SCF), insulin, insulin-like growth factors, such as IGF-2, epidermal growth factor (EGF), and fibroblast growth factor (FGF), such as FGF-1, FLT-3/FLK-2 ligand, granulocyte-macrophage colony-stimulating factor (GM-CSF), granulocyte colony-stimulating factor (G-CSF), and macrophage colony stimulating factor (M-CSF). Growth factors are typically used at concentrations of between picogram/ml to milligram/ml levels.

"Immunophenotype" of a cell is used herein to refer to the phenotype of a cell in terms of the surface protein profile of a cell.

An "isolated cell" refers to a cell which has been separated from other components and/or cells which naturally accompany the cell in a tissue or mammal.

As used herein, a "substantially purified cell" is a cell that has been purified from other cell types with which it is normally associated in its naturally-occurring state.

"Expandability" is used herein to refer to the capacity of a cell to proliferate, for example, to expand in number or, in the case of a population of cells, to undergo population doublings. Cells are expanded in culture when they are placed in a growth medium under conditions that facilitate cell growth and/or division, resulting in a larger population of the cells.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like. The rate of cell proliferation is typically measured by the amount of time required for the cells to double in number, otherwise known as the doubling time.

As used herein, "cell culture" refers to the process whereby cells, taken from a living organism, are grown under controlled conditions.

A "primary cell culture" refers to a culture of cells, tissues or organs taken directly from an organism and before the first subculture.

As used herein, "subculture" refers to the transfer of cells from one growth container to another growth container.

As used herein, a "passage" refers to a round of subculturing. Thus, when cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but, not limited to, the seeding density, substrate, medium, and time between passaging.

As used herein, the term "non-immunogenic" refers to the property of a cell to not induce proliferation of T cells, either in vitro in a mixed lymphocyte reaction (MLR) or in vivo.

As used herein, "tissue engineering" refers to the process of generating tissues ex vivo for use in tissue replacement or reconstruction. Tissue engineering is an example of "regenerative medicine", which encompasses approaches to the repair or replacement of tissues and organs by incorporation of cells, gene or other biological building blocks, along with bioengineered materials and technologies.

As used herein "endogenous" refers to any material produced within or originating inside an organism, cell or system.

"Exogenous" refers to any material introduced into or produced outside an organism, cell, or system.

As used herein, the term "phenotypic characteristics" should be construed to mean at least one of the following characteristics: morphological appearance, the expression of a specific protein, a staining pattern, including, but not limited to, a cytoplasmic staining pattern, specific cell associated enzymatic activity, and the ability to be stained with a substance.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The phrase "under transcriptional control" or "operatively linked" as used herein means that the promoter is in the correct location and orientation in relation to the polynucleotides to control RNA polymerase initiation and expression of the polynucleotides.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (i.e., naked or contained in liposomes) and viruses that incorporate the recombinant polynucleotide.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

As used herein, a "blood disorder" refers to any condition, chronic or acute, in which a subject lacks or has a medically-significant reduced number of at least one type of mature, functional blood cell, including but not limited to, monocyte, macrophage, neutrophil, basophil, eosinophil, T-cell, B-cell, NK-cell, erythrocyte, megakaryocyte and dendritic cells. The condition may be chronic or acute. The underlying cause of the condition may be known, such as but not limited to, chemically-induced or genetically-induced, or the underlying cause may be unknown or uncertain (i.e. idiopathic). Blood disorders encompass hyperproliferative disorders and hypoproliferative disorders that are accompanied or characterized by an insufficient number of at least one type of mature blood cell.

By "pharmaceutically acceptable carrier" is meant any carrier, diluent or excipient which is compatible with the biological component of a pharmaceutical composition and not deleterious to the recipient.

DESCRIPTION OF THE INVENTION

In the present invention, it is demonstrated that CD34$^+$ cells, ALDH$^{br}$ cells and ABCG2-expressing cells are obtained in high quantity from adipose tissue. It is further shown that the cells obtained comprise a variety of subpopulations characteristic of HSCs. Non-limiting examples of the subpopulations include an ALDH$^{br}$SSC$^{lo}$ cell, a CD34$^+$SSC$^{lo}$ cell, a CD34$^+$ALDH$^{br}$ cell, a CD34$^+$CD38$^-$CD41$^-$ cell, a CD34$^+$CD38$^-$CD41$^-$ ALDH$^{br}$ cell, a CD34$^+$CD38$^-$CD41$^-$ SSC$^{lo}$ cell, a CD34$^+$CD45$^-$ cell, a CD34$^+$CD45$^+$ cell, and a CD34$^+$ALDH$^{br}$SSC$^{lo}$ cell. It is further shown that the CD34$^+$ cells obtained comprise a variety of multipotential hematopoietic progenitors and lineage-committed hematopoietic progenitors. Thus, the invention provides a method of isolating in high yield a population of CD34$^+$ cells, ALDH$^{br}$ cells or ABCG2-expressing cells, comprising HSCs, from adipose tissue. The invention further provides a composition of CD34$^+$ cells, ALDH$^{br}$ cells, or ABCG2-expressing cells, comprising HSCs, isolated by the method of the invention to yield a highly enriched population of HSCs as a primary culture. The invention further provides a method of treating a subject in need of HSCs. Advantageously, therefore, the method and composition of the invention reduce or preclude the need for expansion of isolated CD34+ cells, ALDH$^{br}$ cells, or ABCG2-expressing cells, comprising HSCs, prior to use in a therapeutic treatment.

Adipose tissue offers an advantageous alternative to bone marrow or umbilical cord blood as a source of multipotential hematopoietic stem cells. Adipose tissue is readily accessible and abundant in many individuals. Indeed, obesity is a condition of epidemic proportions in the United States, where over 50% of adults exceed the recommended body mass index (BMI) based on their height and weight. Adipose tissue can be harvested by liposuction on an outpatient basis. Liposuction is a minimally non-invasive procedure with cosmetic effects, which are acceptable to the vast majority of patients. Furthermore, it is well documented that adipocytes are a replenishable cell population. Indeed, it is common to see a recurrence of adipocytes in an individual over time at the same site. Therefore, those who do not appreciate the initial cosmetic effect of adipose tissue removal should be nonetheless amenable to the procedure.

In marked contrast to traditional sources, including bone marrow, peripheral blood and umbilical cord blood, it has been discovered that adipose tissue is a rich source of CD34+ cells, ALDH$^{br}$ cells and ABCG2-expressing cells. Specifically, it is shown herein that SVF cells obtained from human adipose tissue comprise at least about 5% and possibly at least about 10% CD34+ cells, comprising HSCs. It is further shown that at least about 40% to about 60% of nonadherent SVF cells are CD34+. It is shown that at least about 10% to about 20% of nonadherent SVF cells are ALDH$^{br}$. It is also shown that at least about 10% to about 20% of nonadherent SCF cells are ABCG2-expressing cells. These high percentages permit the remarkably high yield of CD34+ cells, ALDH$^{br}$ cells or ABCG2-expressing cells, comprising HSCs, that can be obtained from modest quantities of adipose tissue. In one embodiment of the method of the invention, for instance, at least about $1 \times 10^7$ CD34+ cells can be isolated from about 100 milliliters (ml) of adipose tissue from a liposuction procedure. In contrast, 100 ml of bone marrow or cord blood typically yields only about $1-2 \times 10^6$ CD34+ cells.

A typical cosmetic liposuction procedure generates about 3 to about 4 liters of lipoaspirate. Using the method of the invention, this quantity of adipose tissue would potentially yield at least about $3-4 \times 10^8$ CD34+ cells, without requiring prolonged culturing or expansion. In a typical HSC transplantation procedure, about $2 \times 10^6$ CD34+ cells per kilogram body weight is required to be infused into a recipient to achieve a rapid engraftment. A 100 kg person therefore requires about $2 \times 10^8$ CD34+ cells. Thus, the yield from a single liposuction aspirate is potentially sufficient to treat and engraft an averaged-sized adult. Consequently, adipose tissue may be the most clinically relevant and richest source of HSCs identified to date.

The compositions and methods of the instant invention have myriad useful applications. The method of the invention is useful for the preparation of large quantities of CD34+ cells, comprising HSCs, ALDH$^{br}$ cells, comprising HSCs, or ABCG2-expressing cells, comprising HSCS, rapidly and without requiring expansion or multiple passaging to achieve sufficient numbers of HSCs for therapeutic applications. The composition of adipose-derived hematopoietic stem cells may be used in therapeutic methods for alleviating or treating blood disorders in an individual. The composition and method may also be used for research purposes, including, but not limited to, identifying compounds that affect expansion or differentiation of HSCs.

I. Isolating HSCs from Adipose Tissue

The adipose tissue useful in the invention may be obtained from any mammal using any method known to the skilled artisan. Mammals useful as sources of adipose tissue in the methods of the invention include, but are not limited to, cattle, sheep, goats, dogs, horses, cats, non-human primates and humans. Preferably, adipose tissue is isolated from a primate and, more preferably, a human. Preferably, the adipose tissue is subcutaneous white adipose tissue. A preferred source of adipose tissue is omental adipose. In humans, adipose is typically isolated by liposuction. If the cells of the invention are to be transplanted into a human subject, it is preferable that the adipose tissue be isolated from that same subject so as to provide for an autologous transplant, or from a genetically-identical sibling (e.g. identical twin) to provide for a syngeneic transplant. Alternatively, however, the administered HSCs may be allogenic.

According to one embodiment of the invention, adipose-derived HSCs are isolated by isolating the CD34+, nonadherent cells of the SVF. In another embodiment, HSCs are isolated from adipose tissue by isolating the ALDH$^{br}$ nonadherent cells of the SVF. In one aspect, ALDH$^{br}$SSC$^{lo}$ nonadherent SVF cells, comprising adipose-derived HSCs, are isolated. In another embodiment, adipose-derived HSCs are isolated by isolating the ABCG2-expressing, nonadherent cells of the SVF.

Any method known to the skilled artisan for preparing SVF from adipose tissue may be used in practicing the invention. For example, such methods are described in U.S. Pat. No. 6,153,432 incorporated herein in its entirety. Typically, the adipose tissue is treated with collagenase at concentrations between 0.01 to 0.5%, preferably 0.04 to 0.3%, most preferably about 0.2%, trypsin at concentrations between 0.01 to 0.5%, preferably 0.04%, most preferably about 0.2%; and/or dispase at concentrations of 0.5 ng/ml to 10 ng/ml; and/or effective concentrations of hyaluronidase or DNase; and ethylenediaminetetra-acetic acid (EDTA) at concentrations of about 0.01 to 2.0 mM, preferably at about 0.1 to about 1.0 mM, most preferably at 0.53 mM; at temperatures between 25° to 50° C., preferably between 33° to 40° C., most preferably at 37° C., for periods of between 10 minutes to 3 hours, preferably between 30 minutes to 1 hour, most preferably 45 minutes. Optionally, the cells are passed through a nylon or cheesecloth mesh filter of between 20 microns to 800 microns, more preferably between 40 to 400 microns, most preferably 70 microns. The cells are then subjected to differential centrifugation directly in media or over a Ficoll or Percoll or other particulate gradient. Cells will be centrifuged at speeds of between 100 to 3000×g, more preferably 200 to 1500×g, most preferably at 500×g for periods of between 1 minutes to 1 hour, more preferably 2 to 15 minutes, most preferably 5 minutes, at temperatures of between 4° to 50° C., preferably between 20° to 40° C., most preferably at about 25° C. This cell pellet is the SVF. The SVF cell pellet is plated to obtain nonadherent cells.

Nonadherent cells of the SVF are isolated by first incubating the SVF cells in stromal cell medium in a culture apparatus for a period of time. A "period of time" can be any time suitable for the culture of cells in vitro and allowing adherent cells to adhere. In one embodiment, the period of time is about 12 hours. In a preferred embodiment, the period of time is 24 hours. The culturing apparatus can be any culture apparatus commonly used in culturing cells in vitro. A preferred culture apparatus is a culture flask, with a more preferred culture apparatus being a T-225 culture flask. Plating density may range from about 10,000 cell per cm$^2$ to about 100,000 cell per cm$^2$. In one embodiment, cells are plated in a culture flask at about 50,000 cells per cm$^2$ and any whole integer therebetween. However, the invention is not limited by the plating density. The skilled artisan can determine appropriate plating density with routine experimentation.

The nonadherent cells comprising the HSCs are collected from the culture apparatus at any time during the culturing. A non-limiting method of collecting the nonadherent cells comprises withdrawing the liquid media from the culture apparatus. The medium may be replaced during the culture of the SVF cells at any time; the removed medium comprising nonadherent SVF cells (and therefore HSCs) can be collected daily up to the first passage trypsinization. Preferably, the stromal cell medium is replaced every 3 to 4 days.

If desired, adipose tissue-derived stromal cells (ASCs), present in the adherent fraction, are also harvested from the culture apparatus. The ASCs can be used immediately or cryopreserved to be stored for use at a later time. Adipose tissue derived-stromal cells may be harvested by trypsinization, EDTA treatment, or any other procedure used to harvest adherent cells from a culture apparatus. Adipose tissue-derived stromal cells may be administered to a subject receiving HSCs, for instance, to provide hematopoietic support cells to aid in engraftment of the HSCs.

HSCs may be characterized by any method known to the skilled artisan. The immunophenotype of HSCs can be exploited to serve as unique identifiers for HSCs. That is, the unique cell surface markers on the cells of interest can be used to isolate a specific sub-population of cells from a mixed population of cells derived from adipose tissue. Phenotypic markers of HSCs are well known to those of ordinary skill in the art, and copiously published in the literature. Additional phenotypic markers continue to be disclosed or can be identified without undue experimentation. Some phenotypic markers specific for HSCs include CD34, CD45, CD38$^{lo/-}$, CD41, and ABCG2. Other characteristics of HSCs are high aldehyde dehydrogenase (ALDH$^{br}$) activity and low side scatter (SSC$^{lo}$). Other markers for HSCs and various hematopoietic committed lineages include CD2, CD3, CD4, CD5, CD6, CD7, CD8, CD13, CD14, CD15, CD19, CD20, CD32, CD51, CD52, CD53, CD56, CD57, CD60, CD61, CD62L, CD65, CD72, CD73, CD81, CD82, CD83, CD90, CD99, CD100, CD117, TCR, P-selectin, HLA-DR, etc. One of ordinary skill in the art will recognize that known colorimetric, fluorescent, immunochemical, polymerase chain reaction, chemical or radiochemical methods can readily ascertain the presence or absence of a lineage specific marker or enzymatic activity.

Preferably, the adipose-derived HSCs are characterized by cell surface expression of CD34, high ALDH activity (ALDH$^{br}$), light scatter properties (e.g. SSC$^{lo}$) and/or ABCG2 expression. The nonadherent cells isolated from the SVF comprise at least about 10% CD34$^+$ cells, preferably at least about 20% CD34$^+$ and more preferably at least about 40% CD34$^+$ cells. The nonadherent cells isolated from the SVF comprise at least about 10% ALDH$^{br}$ cells, preferably at least about 15% ALDH$^{br}$ and more preferably at least about 20% ALDH$^{br}$ cells. The nonadherent cells isolated from the SVF comprise at least about 10% ABCG2-expressing cells, preferably at least about 15% ABCG2-expressing cells and more preferably at least about 20% ABCG2-expressing cells cells.

One skilled in the art will further appreciate that an antibody specific for a cell surface marker can be conjugated to a physical support (i.e. a streptavidin bead) and, therefore, be used to bind and isolate HSCs having that specific cell surface marker. An example of an antibody that specifically binds to an HSC includes, but is not limited to, an anti-CD34$^+$ antibody. After binding, the bound HSCs can be separated from the remaining cells by, for instance, magnetic separation using magnetic beads, including but not limited to Dynabeads® (Dynal Biotech, Brown Deer, Wis.). Further to the use of Dynabeads®, MACS separation reagents (Miltenyi Biotec, Auburn, Calif.) can be used to remove HSCs from a mixed population of cells. Alternatively, the immunophenotype, the light scatter properties, and/or the presence of a detectable HCS-characteristic enzyme product of HSCs permit sorting using a flow cytometry-based cell sorter. As a result of the separation step or cell sorting, a population of CD34$^+$ cells, ALDH$^{br}$ cells and/or ABCG2-expressing cells, enriched for HSCs, is obtained. In an embodiment, the population of HSCs is a purified cell population. The isolated HSCs can be used immediately in therapeutic applications without further expansion, can be cryopreserved using techniques known in the art or can be cultured and expanded and, optionally, differentiated in vitro using methods disclosed herein or conventional methods.

HSCs may also be characterized by performing colony forming assays to assess multipotential and lineage-committed hematopoietic progenitors. Any method known to the skilled artisan for performing colony forming assays may be used. Preferably, the HSCs in nonadherent cells isolated from the SVF comprise colony-forming unit granulocyte macrophages (CFU-GM), burst-forming unit erythrocytes (BFU-E) and colony-forming unit granulocyte erythrocyte macrophage megakaryocytes (CFU-GEMM).

A medium useful for culturing ASCs is referred to herein as "stromal cell medium". A medium useful for culturing HSCs is referred to herein as "hematopoietic stem cell medium". Any medium capable of supporting fibroblasts in cell culture may be used as a stromal cell medium, a hematopoietic stem cell medium or as a medium for the co-culture of ASCs and HSCs. Typically, a stromal cell medium or a hematopoietic stem cell medium comprises a base medium, serum and an antibiotic/antimycotic. A non-limiting example of a stromal cell medium is a medium comprising DMEM/F 12 Ham's, 10% fetal bovine serum (FBS), 100 U/ml penicillin, 100 μg/ml streptomycin (Pen-Strep) and 0.25 μg/ml amphotericin B. An non-limiting example of a hematopoietic stem cell medium is a medium comprising DMEM, 10% fetal bovine serum (FBS), 4 mM L-glutamine, 50 mg/ml penicillin and streptomycin, and 100 ng/ml each of Flt-3 ligand, stem cell factor and megakaryocyte growth and development factor (MGDF). Another example of a hematopoietic stem cell medium is Iscove's medium with 2% FBS. This medium is useful, for instance, in diluting cells for CFU assays. However, ASCs and HSCs may be cultured in a base medium supplemented with at least one growth factor, cytokine or hormone and without an antibiotic/antimycotic.

Media useful in the isolation and propagation of HSCs according to the methods of the invention are known in the art. These media are also useful in isolation and propagation of ASCs. Non-limiting examples of base media useful in the methods of the invention include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA, and Biological Industries, Bet HaEmek, Israel, among others. A number of these media are summarized in Methods in Enzymology, Volume LVIII, "Cell Culture", pp. 62-72, edited by William B. Jakoby and Ira H. Pastan, published by Academic Press, Inc. Sigma-Aldrich, Stemcell Technologies, StemGenix, Mabio and Quality Biological Inc., among others, offer proprietary media for propagation of hematopoietic stem cells.

Sera useful in the invention include, but are not limited to, fetal serum of bovine or other species at a concentration of at least 1% to about 30%, preferably at least about 5% to 15%, mostly preferably about 10%. Embryonic extract of chicken or other species can be present at a concentration of about 1% to 30%, preferably at least about 5% to 15%, most preferably about 10%. In some therapeutic embodiments for humans, the use of non-human_sera may not be desired, due to safety risks of possible transmission of adventitious infectious contaminants in sera. The skilled medical practitioner is familiar with medically-appropriate handling of HSCs for therapeutic applications.

By "growth factors, cytokines, hormones" is intended the following specific factors including, but not limited to, erythropoietin (EPO), macrophage colony stimulating factor, thrombopoietin (TPO), growth hormone (GH), interleukin 1-α and 1-β, interleukin 3 (IL-3), interleukin 4 (IL-4), interleukin 5 (IL-5), interleukin 6 (IL-6), interleukin 7 (IL-7), interleukin 9 (IL-9), interleukin 10 (IL-10), interleukin 11 (IL-11), interleukin 13 (IL-13), c-kit ligand/stem cell factor (SCF), insulin, insulin-like growth factors, such as IGF-2, leukemia inhibitory factor (LIF), macrophage inhibitory protein 1α (MIP 1α), epidermal growth factor (EGF), and fibroblast growth factor (FGF), such as FGF-1, FLT-3/FLK-2 ligand, megakaryocyte growth and development factor (MGDF), granulocyte-macrophage colony-stimulating factor (GM-CSF), granulocyte colony-stimulating factor (G-CSF), and macrophage colony stimulating factor (M-CSF) at concentrations of between picogram/ml to milligram/ml levels. Factors useful for expansion of HSCs include, but are not limited to, IL-3, SCF, FLT-3/FLK-2 ligand, IL-6 and GM-CSF. When HSCs are to be administered in a therapeutic application to a human, any growth factor, cytokine and/or hormone in the media is preferably human.

It is further recognized that additional components may be added to the culture medium. Such components may be antibiotics, antimycotics, albumin, amino acids, and other components known to the art for the culture of cells. Additionally, components may be added to enhance the differentiation process. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 μg/ml. However, the invention should in no way be construed to be limited to any one medium for culturing stromal cells and/or HSCs. Rather, any media capable of supporting adipose tissue SVF cells and HSCs in tissue culture may be used.

Adipose-derived HSCs, isolated as described herein, may be cryopreserved according to routine procedures. Preferably, about one to ten million cells are cryopreserved in stromal cell medium containing 10% DMSO in vapor phase of liquid $N_2$. Frozen cells may be thawed by swirling in a 37° C. bath, resuspended in fresh growth medium, and expanded as described above.

II. Using HSCs

The adipose-derived HSCs obtained by the method of the invention may be used in any method known in the art for using HSCs. Additionally, the HSCs may be used in methods and compositions yet to be discovered. One method of using the HSCs is administering them to a recipient subject in need of HSCs.

The recipient subject may be any mammal, including horse, goat, cattle, dog, sheep, cat, non-human primate, and human. Preferably, the recipient subject is a human. The source of the adipose tissue used to obtain HSCs for transplantation may be the same as the recipient subject of therapy (autologous transplantation) or may be from a donor subject. The donor subject may be genetically identical to the recipient subject (syngeneic transplantation) or may be a non-genetically identical subject of the same species (allogeneic transplantation).

Disorders that can be treated by infusion of the disclosed cells include, but are not limited to, diseases resulting from a failure of a dysfunction of normal blood cell production and maturation (i.e., aplastic anemia and hypoproliferative stem cell disorders). The administration of HSCs is intended to supplement or replace flawed endogenous blood cell production and maturation. Such disorders may generally be neoplastic, malignant diseases in the hematopoietic organs (e.g., leukemia and lymphomas); broad spectrum malignant solid tumors of non-hematopoietic origin; autoimmune conditions; or genetic disorders. Such disorders include, but are not limited to diseases resulting from a failure or dysfunction of normal blood cell production and maturation, hyperproliferative stem cell disorders, including aplastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type I, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportions in lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antitrypsin deficiency, among others.

The cells may be administered to a recipient subject in a wide variety of ways. Preferred modes of administration are parenteral, intraperitoneal, intravenous, intradermal, epidural, intraspinal, intrastemal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere. A preferred method of administration is intravenous infusion. Methods for bone marrow transplants are well known in the art and are described in, for example, U.S. Pat. No. 4,678,470, and U.S. Pat. No. 5,571,083, teaches methods for transplanting cells to any anatomical location in the body.

In order to transplant the cells of the present invention into a human, the cells are isolated as described herein. The isolated HSCs may be subsequently treated in any way medically necessary for transplantation. Optionally, cells such as T-cells, are removed from the HSCs using methods known in the art. Such methods include, but are not limited to, counterflow centrifugal elutriation, soybean agglutinin/E-rosette formation, density gradient centrifugation and immunological depletion. Methods of purging tumor cells for autologous transplants as part of cancer treatment are also known in the art.

Preferably, the cells to be transplanted are from the subject into which the cells are to be transplanted (autologous transplantation). In the case where cells are not from the patient (allogeneic transplantation), blood type or haplotype compatibility determined between the donor cell and the patient are typically determined. A physician skilled in the art is familiar with compatibility issues in allogeneic transplants.

Between about $10^5$ and about $10^{13}$ CD34$^+$, ALDH$^{br}$ and/or ABCG2-expressing cells per 100 kg person are administered to a human. In some embodiments, between about $1.5 \times 10^6$ and about $1.5 \times 10^{12}$ cells are administered per 100 kg person. In some embodiments, between about $1 \times 10^8$ and about $5 \times 10^{11}$ cells are administered per 100 kg person. In some embodiments, between about $1 \times 10^9$ and about $2 \times 10^{11}$ cells are administered per 100 kg person. In other embodiments, between about $5 \times 10^8$ cells and about $1 \times 10^{10}$ cells are administered per 100 kg person. The cells can be administered to a person by various methods including but not limited to infusion and intravenous administration.

In some embodiments, a single administration of cells is provided. In some embodiments, multiple administrations are provided. In some embodiments, multiple administrations are provided over the course of 3-7 consecutive days. In some embodiments, 3-7 administrations are provided over the course of 3-7 consecutive days. In other embodiments, 5 administrations are provided over the course of 5 consecutive days.

In some embodiments, a single administration of between about $10^5$ and about $10^{13}$ cells per 100 kg person is provided. In some embodiments, a single administration of between about $1.5 \times 10^8$ and about $1.5 \times 10^{12}$ cells per 100 kg person is provided. In some embodiments, a single administration of between about $1 \times 10^8$ and about $5 \times 10^{11}$ cells per 100 kg person is provided. In some embodiments, a single administration of about $1 \times 10^9$ to $1 \times 10^{10}$ cells per 100 kg person is provided. In some embodiments, a single administration of $1 \times 10^{10}$ cells per 100 kg person is provided.

In some embodiments, multiple administrations of between about $10^5$ and about $10^{13}$ cells per 100 kg person are provided. In some embodiments, multiple administrations of between about $1.5 \times 10^8$ and about $1.5 \times 10^{12}$ cells per 100 kg person are provided. In some embodiments, multiple administrations of between about $1 \times 10^8$ and about $5 \times 10^{11}$ cells per 100 kg person are provided over the course of 3-7 consecutive days. In some embodiments, multiple administrations of about $4 \times 10^9$ cells per 100 kg person are provided over the course of 3-7 consecutive days. In some embodiments, multiple administrations of about $2 \times 10^{11}$ cells per 100 kg person are provided over the course of 3-7 consecutive days. In some embodiments, 5 administrations of about $3.5 \times 10^9$ cells are provided over the course of 5 consecutive days. In some embodiments, 5 administrations of about $4 \times 10^9$ cells are provided over the course of 5 consecutive days. In some embodiments, 5 administrations of about $1.3 \times 10^{11}$ cells are provided over the course of 5 consecutive days. In some embodiments, 5 administrations of about $2 \times 10^{11}$ cells are provided over the course of 5 consecutive days.

In another embodiment, the HSCs are treated with a growth factor, cytokine or hormone to induce commitment to a particular differentiated state, prior to their administration. Adipose-derived HSCs can be differentiated in vitro by treating the cells with differentiation factors as described elsewhere herein and by standard methods known in the art.

Partially or terminally differentiated cells may be characterized by the identification of surface and intracellular proteins, genes, and/or other markers indicative of the lineage commitment of the HSCs to a particular terminal differentiated state. These methods will include, but are not limited to, (a) detection of cell surface proteins by immuno-fluorescent methods using protein specific monoclonal antibodies linked using a secondary fluorescent tag, including the use of flow cytometric methods; (b) detection of intracellular proteins by immunofluorescent methods using protein specific monoclonal antibodies linked using a secondary fluorescent tag, including the use of flow cytometric methods; (c) detection of cell genes by polymerase chain reaction, in situ hybridization, and/or northern blot analysis.

In another embodiment, adipose-derived stromal cells (ASCs) are also administered to the recipient subject to provide hematopoietic support cells to assist in the engraftment of the HSCs. The ASCs may be co-infused with the HSCs or may be administered before or after HSC administration. ASCs may be administered using similar dosage guidelines as provided for HSCs.

III. Genetic Modification

In another embodiment, the adipose-derived HSCs of the invention are genetically modified, e.g., to express exogenous genes or coding sequences or to repress or otherwise alter the expression of endogenous genes. Such genetic modification may have therapeutic benefit when the HSCs are administered to a subject. Alternatively, the genetic modification may provide a means to track or identify the so-modified cells, for instance, after transplantation of such genetically-modified, adipose-derived HSCs into a subject. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, $His_6$, and the like).

Tracking the migration, differentiation and integration of the cells of the present invention is not limited to using detectable molecules expressed from a vector or virus. The migration, integration, and differentiation of a cell can be determined using a series of probes that would allow localization of transplanted HSCs. Tracking transplanted cells may further be accomplished by using antibodies or nucleic acid probes for cell-specific markers detailed elsewhere herein.

Therapeutic use of genetically-modified HSCs includes, but is not limited to, providing expression of a protein that is mutated, deficient or otherwise dysfunctional in the patient. For instance, HSCs could be genetically modified to provide hemoglobin A in place of, or in addition to hemoglobin S, for the treatment of sickle cell anemia. Thalassemia and X-Linked Severe Combined Immunodeficiency are other, non-limiting, candidates for gene therapy using HSCs genetically modified ex vivo. A cell expressing a desired isolated nucleic acid can be used to provide the product of the isolated nucleic acid to another cell, tissue, or whole mammal where a higher level of the gene product is useful to treat or alleviate a disease, disorder or condition associated with abnormal expression and/or activity. Therefore, the invention includes an HSC expressing an isolated nucleic acid encoding a desired sequence where increasing expression, protein level, and/or activity of the desired protein can be useful to treat or alleviate a disease, disorder or condition involving the hematopoietic system.

The invention also includes an HSC which, when an isolated nucleic acid is introduced therein, and the protein encoded by the nucleic acid is expressed therefrom, where it was not previously present or expressed in the cell or where it is now expressed at a level or under circumstances different than that before the transgene was introduced, a benefit is obtained. Such a benefit may include the fact that there has been provided a system wherein the expression of the desired nucleic acid can be studied in vitro in the laboratory or in a mammal in which the cell resides, a system wherein cells comprising the introduced nucleic acid can be used as research, diagnostic and therapeutic tools, and a system wherein mammal models are generated which are useful for the development of new diagnostic and therapeutic tools for selected disease states in a mammal.

Thus, the invention encompasses expression vectors and methods for the introduction of exogenous DNA into HSCs with expression of the exogenous DNA in the cells. The skilled artisan is familiar with techniques for generating expression vectors and transforming cells with them. See, for instance, Sambrook et al. (2001, Molecular Cloning: A Laboratory Manual, Cold Spring Harbor Laboratory, New York), and Ausubel et al. (1997, Current Protocols in Molecular Biology, John Wiley & Sons, New York).

The expression vector is a genetic vector suitable for delivering the expression cassette to the cell. Depending on the desired end application, any such vector can be so employed to genetically modify the cells (e.g., plasmids, naked DNA, viruses such as adenovirus, adeno-associated virus, herpesvirus, lentivirus, papillomavirus, retroviruses, etc.). Any method of constructing the desired expression cassette within such vectors can be employed, many of which are well known in the art, such as direct cloning, homologous recombination, etc. The desired vector will largely determine the method used to introduce the vector into the cells, which are generally known in the art. Suitable techniques include protoplast fusion, calcium-phosphate precipitation, gene gun, electroporation, photoporation, DEAE dextran or lipid carrier mediated transfection, and infection with viral vectors.

The expression vector comprises an expression cassette comprising the nucleotide sequence to be expressed operatively linked to expression control sequences, such as a promoter. The nucleotide sequence to be expressed can encode a protein, or it can encode biologically active RNA, such as antisense RNA, siRNA or a ribozyme. Thus, the coding polynucleotide can encode a gene conferring, for example, resistance to a toxin, a hormone (such as peptide growth hormones, hormone releasing factor, and cytokines such as interferons, interleukins, and lymphokines), a cell surface-bound intracellular signaling moiety (such as cell-adhesion molecules and hormone receptors), and factors promoting a given lineage of differentiation, or any other coding sequence.

Examples of suitable promoters include prokaryotic promoters and viral promoters (e.g., retroviral ITRs, LTRs, immediate early viral promoters (IEp), such as herpesvirus IEp (e.g., ICP4-IEp and ICP0-IEEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Isolation of Hematopoietic Stem Cells from Lipoaspirate Adipose Tissue

Adipose tissue was obtained from liposuction lipoaspirate performed on human subjects for cosmetic reasons. A 50 milliliter (ml) lipoaspirate material was washed by mixing with 50 ml PBS (phosphate buffered saline) and aspirating the aqueous layer below the fat. The cell suspension was washed twice more with PBS, until the wash was straw colored. The aqueous washes were pooled and saved as "aspirate post-wash pellet" (APWP). Fifty (50) ml of 95 mg collagenase dissolved in 50 ml PBS+1% bovine serum albumin (BSA) was added to the washed cell suspension and the mixture was transferred to a T-185 flask. The flask was incubated at 37° C. on a Belly Dancer® shaker (Stovall Life Science, Greensboro, N.C.) for 1 hour.

The dissolved fat was centrifuged at approximately 550×g (1600 rpm) for 6 minutes. The top, fatty layer, about 10-20 ml, was poured off. The cell pellet was resuspended in the remaining supernatant and poured through a 100 micrometer cell strainer to remove debris. The flow-through was centrifuged at approximately 550×g (1600 rpm) for 6 minutes to pellet the cells. The supernatant was discarded.

The cell pellet was suspended in red cell lysis buffer (eBioscience). The suspended cells were put on ice for 3 minutes, then centrifuged at approximately 550×g (1600 rpm) for 6 minutes. The supernatant was discarded. (Subsequent work indicated that the red cell lysis step was not necessary or desirable for isolating HSCs from SVF.)

The cell pellet was suspended in PBS to wash the cells, and the cells were pelleted as above. The pellet was then suspended in 5 ml culture medium (DMEM/F12 Ham's supplemented with 10% fetal bovine serum, penicillin, streptomycin and antibiotics and 0.25 microgram (µg) per ml amphotericin B). These cells are the "unfractionated SVF".

The unfractionated SVF cells were counted and viability was determined using trypan blue exclusion. The cells were then plated at approximately 50,000 live cells per cm$^2$ in T-185 flasks.

The flasks were incubated in a 37° C. incubator at 5% CO$_2$. After 24 hours, the culture medium, containing the nonadherent cells, was removed and replaced with fresh culture medium. The nonadherent cell fraction was retained as "nonadherent SVF".

The surface immunotype of the nonadherent SVF cells was characterized by flow cytometry. Expression of CD34 and CD45, classic markers of HSCs, was examined first. As shown in FIG. 1, center panel, about 40.88% of the nonadherent SVF cells from this adipose tissue sample were found to express CD34$^+$, a well-known marker for HSCs. (Experiments with adipose tissue from other donors indicated that up to about 50% to about 60% of nonadherent SVF cells express CD34+.) These data indicated that a yield of at least about 1×10$^7$ CD34$^+$ cells is possible from about 100 ml of human adipose tissue.

Multiple CD34$^+$ subpopulations were observed in the nonadherent SVF population. There were two distinct side scatter populations observed for this representative donor, a low CD34$^+$ (CD34$^{lo}$) and a high CD34$^+$ (CD34$^{hi}$). CD34$^{hi}$ cells comprised about 27.2% (23%+4.29%) of the nonadherent SVF cells and CD34$^{lo}$ comprised about 13.59% (8.88%+4.71%). The population of CD34$^{hi}$CD45$^-$ comprised about 23% of the cells. The CD34$^{lo}$CD45$^-$ population comprised about 8.88% of the nonadherent SVF cells. The CD34$^+$CD45$^+$ population comprised about 9% of the nonadherent SVF cells (4.29%+4.71%).

Back-gating was also performed to examine the forward and side scatter of the various CD34$^+$ subpopulations. This analysis revealed that several distinct side scatter groups are present (FIG. 1, two panels on left and two panels on right). The CD34$^{hi}$ population (top left and top right panels) was found to have a lower side scatter (SSC$^{lo}$), compared to the CD34$^{lo}$ population (bottom left and bottom right panels). Low side scatter is typically associated with hematopoietic stem cell populations.

Figure 2:
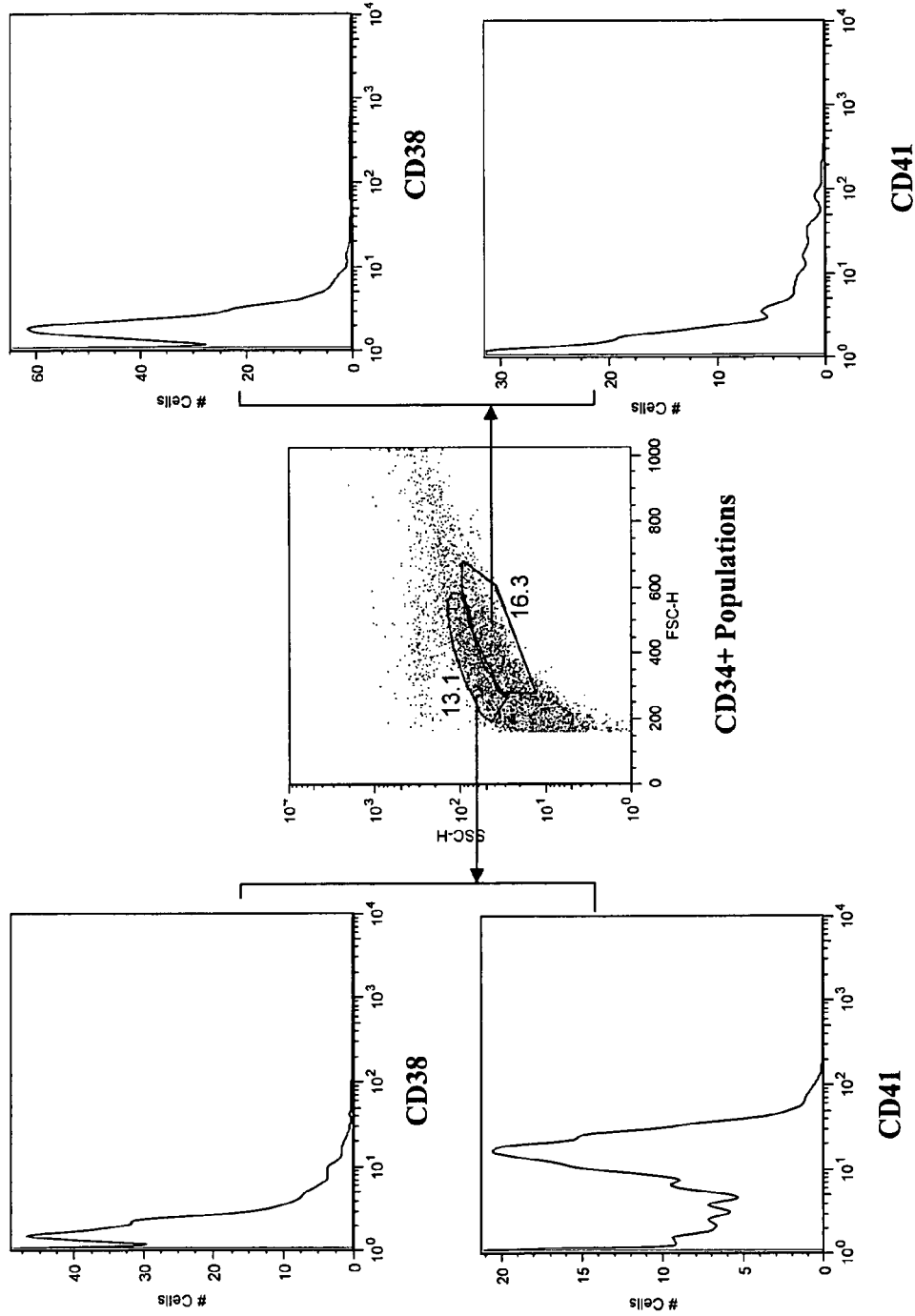
FIG. 2 is a series of plots of flow cytometry data regarding expression of CD38 and CD41 for two major populations of $CD34^+$ cells (low side scatter and high side scatter) isolated from adipose tissue nonadherent SVF. The two plots on the right side are of low side scatter, $CD34^+$ cells.

CD38 and CD41 are cell surface markers that have been used to identify subpopulations of CD34$^+$ cells and are moderately useful in predicting improved HSC engraftment. CD41 expression indicates the start of hematopoiesis and is also used to distinguish between endothelial progenitors (CD34$^+$CD41$^+$ cells) and HSCs (CD34$^+$CD38$^-$CD41$^-$ cells) in mixed populations of CD34$^+$ cells. As shown in FIG. 2 (left two panels), the high side scatter CD34$^+$ population, comprising about 13% of the nonadherent SVF population, contained a significant number of CD41+ cells. Notably, the low side scatter CD34$^+$ population (~16% of the nonadherent SVF population) lacked expression of both CD38 and CD41, consistent with the immunophenotype typical of HSCs.

Figure 3:
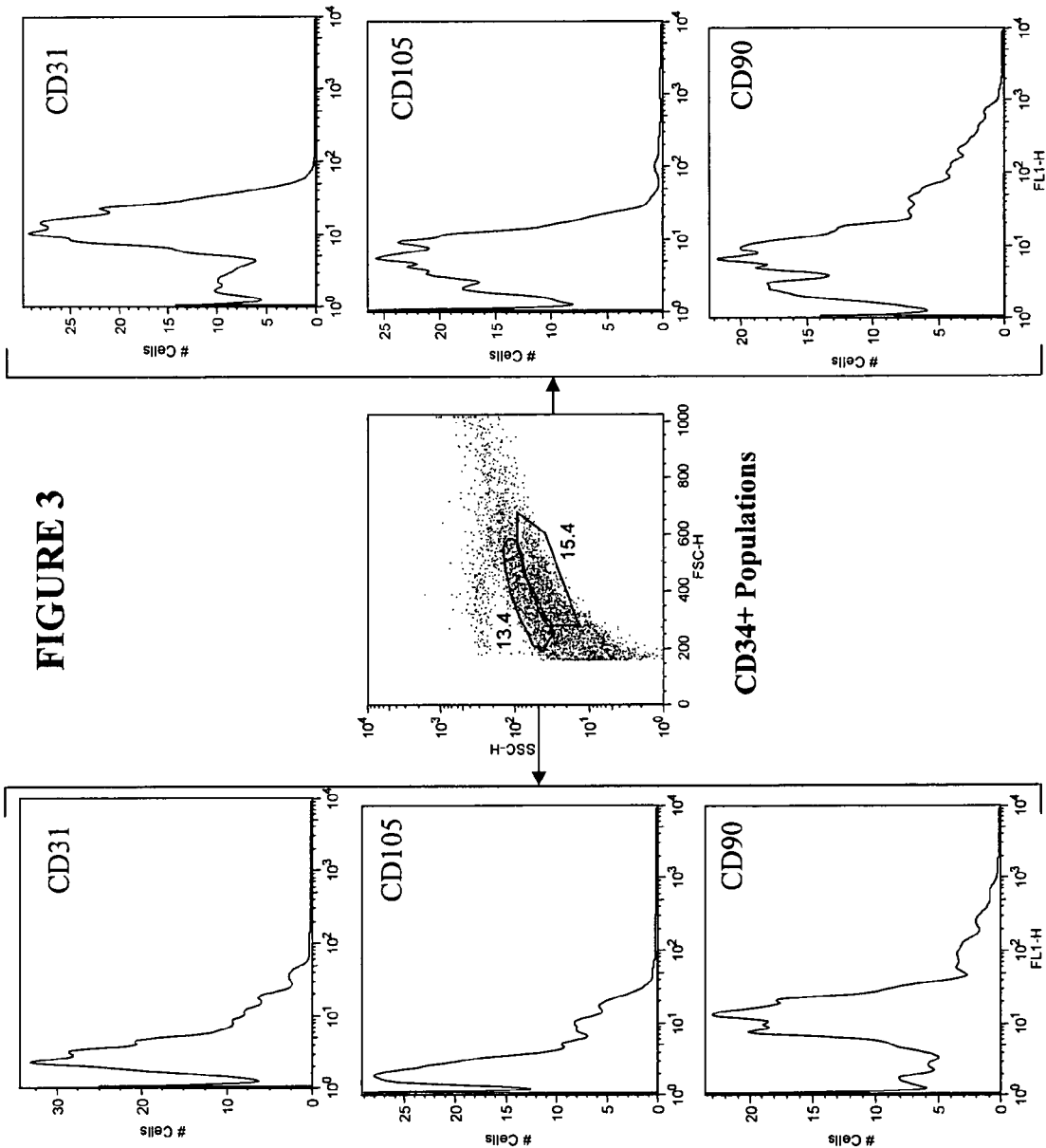
FIG. 3 is a series of plots of flow cytometry data regarding expression of CD31, CD105 and CD90 for two major populations of $CD34^+$ cells isolated from adipose tissue nonadherent SVF. The three plots on the right side are of low side scatter, $CD34^+$ cells.

Following the identification of the two major populations of CD34$^+$ cell in the light scatter acquisition dot plot, the cells were gated separately to determine if endothelial (CD31) or stromal markers (CD105 and CD90) were co-expressed with CD34. Though CD90 can also be expressed on hematopoietic cells, Endogin (CD105) is exclusively a stromal lineage marker. As shown in FIG. 3, various levels of co-expression and lineage negative populations were observed in CD34$^+$ cells with low side scatter and CD34+ cells with high side scatter. CD31 and CD105 are not expected to be expressed on CD34+ HSCs. CD34+CD31+ cells and CD34+CD105+ cells are likely to be endothelial and stromal cell lineages.

Thus, the nonadherent SVF cells comprised multiple permutations of different phenotypic marker expressions within the heterogeneous mix including: a CD34+ SSC$^{lo}$ population, a CD34$^+$ SSC$^{lo}$ population, a CD34$^{hi}$ SSC$^{lo}$ population, a CD34$^{hi}$CD38$^-$CD41$^-$SSC$^{lo}$ population; a CD34$^{lo}$CD45$^-$ population; and a CD34$^{lo}$CD45$^+$ population. Expression of c-kit (CD117), a marker also associated with HSCs, was also observed on approximately 2-3% of the nonadherent SVF cells.

Expression of ABCG2, another HSC marker, was observed on about 16% of the nonadherent SVF cells (FIG. 8B). Advantageously, nonadherent SVF cells having bright ABCG2 fluorescence have a discrete light scatter profile. In FIG. 8A, the circled region of cells, representing about 25% of the total cells, include the cells having bright ABCG2 fluorescence. This feature allows for the possibility of enriching for these cells based only on light scatter data and without the use of antibodies or any other chemical manipulation. Thus, the nonadherent SVF comprises cells that exhibit immunophenotypes and differentiation potential comparable to bone marrow-derived HSCs.

Colony forming unit assays use limit dilution methods to quantify the frequency of specific lineage progenitors. Separate populations of cells labeled as the "aspirate post wash pellet" (APWP) the "unfractionated SVF" and the "nonadherent SVF" were plated in Methocult® Media (Stem Cell Technologies, Vancouver, Canada) to assay for the existence of hematopoietic colony forming progenitors. The various cell fractions were plated at two cell concentrations, 25,000 cells per ml and 50,000 cells per ml. A 1.1 ml aliquot of Methocult media cell suspension was added to duplicated 35 mm culture dishes. After 14 days in the culture, the number of CFUs per plate was counted and analyzed to determine the frequency of BFU-E, CFU-GM and CFU-GEMM colonies. The results of one experiment are shown in Table 1.

Figure 4:
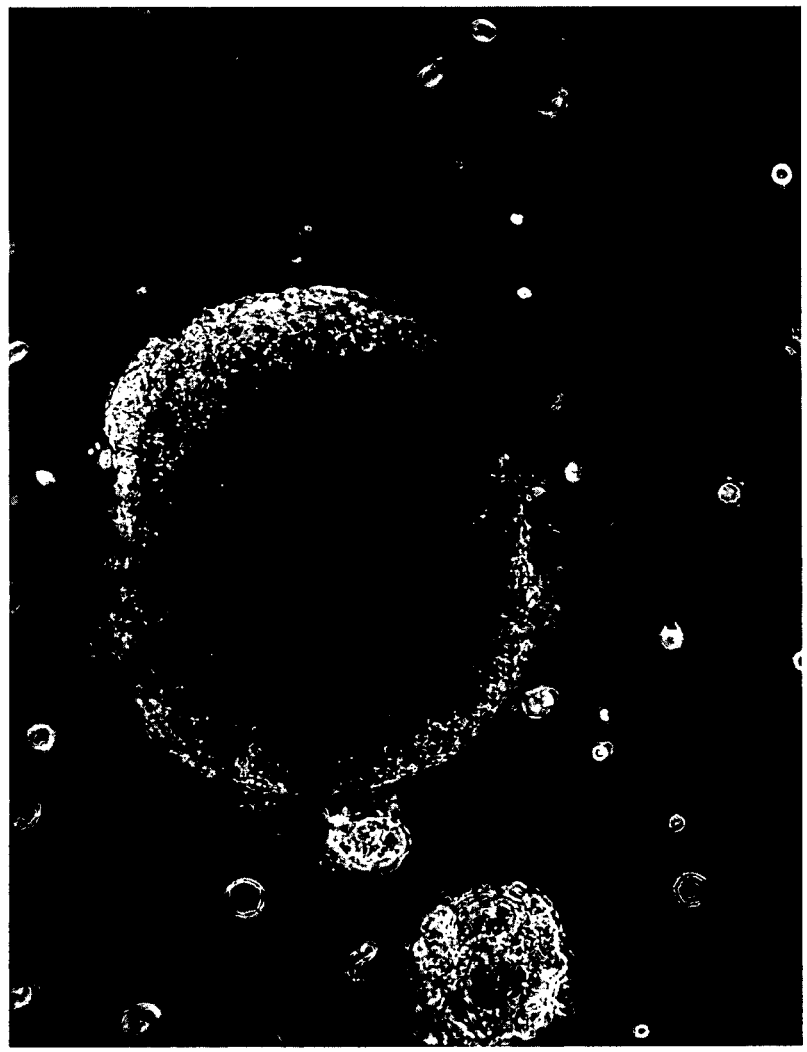
FIG. 4 is an image of a BFU-E colony at Day 14 of the Methocult® (Stem Cell Technologies) culture. The colonies were observed following culture of 20,000 nonadherent SVF cells (100× magnification).
Figure 5:
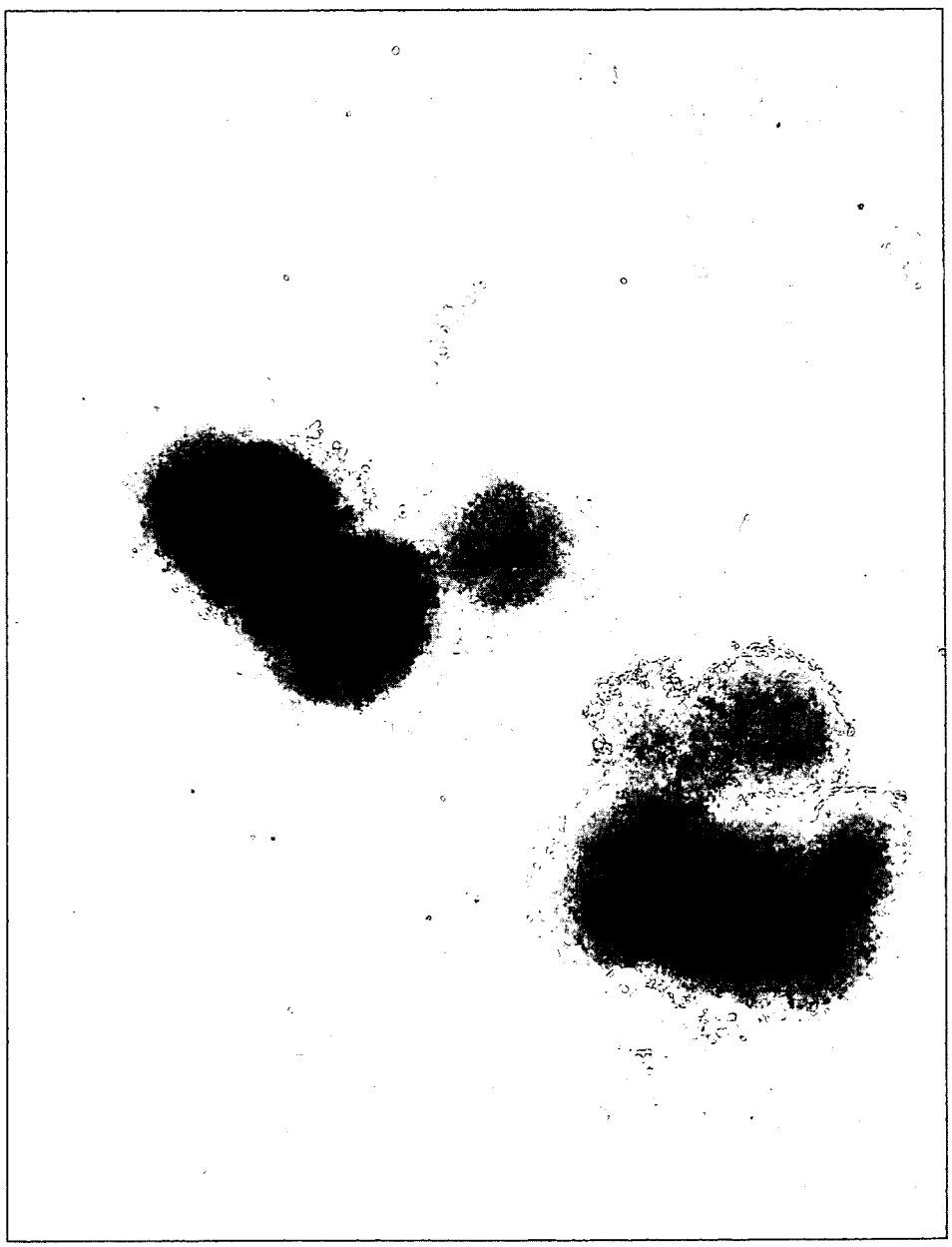
FIG. 5 is an image of two BFU-E colonies at Day 14 following culture of 20,000 nonadherent SVF cells (100× magnification).
Figure 6:
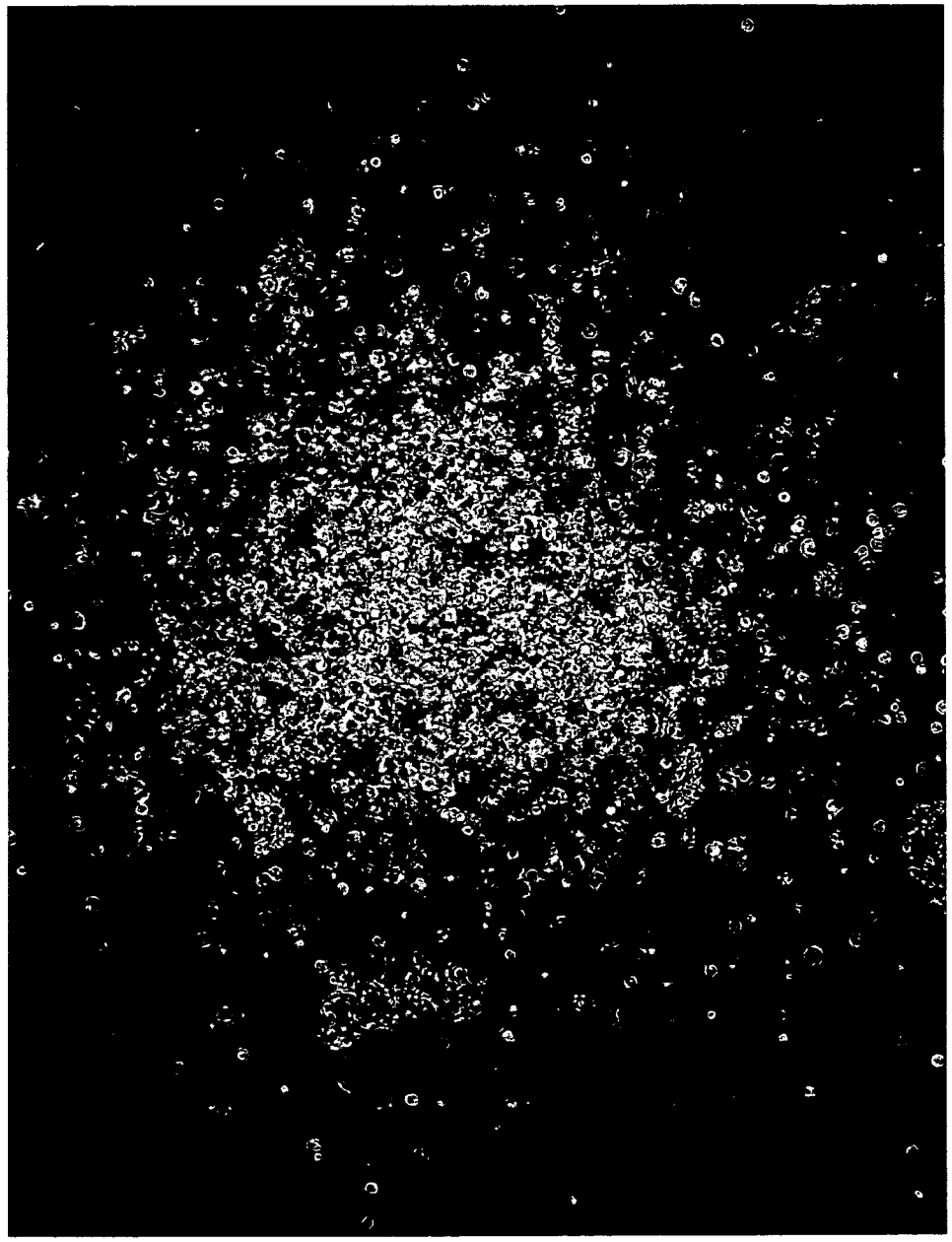
FIG. 6 is an image of a CFU-GM colony at Day 14 following culture of 20,000 nonadherent SVF cells (100× magnification).
Figure 7:
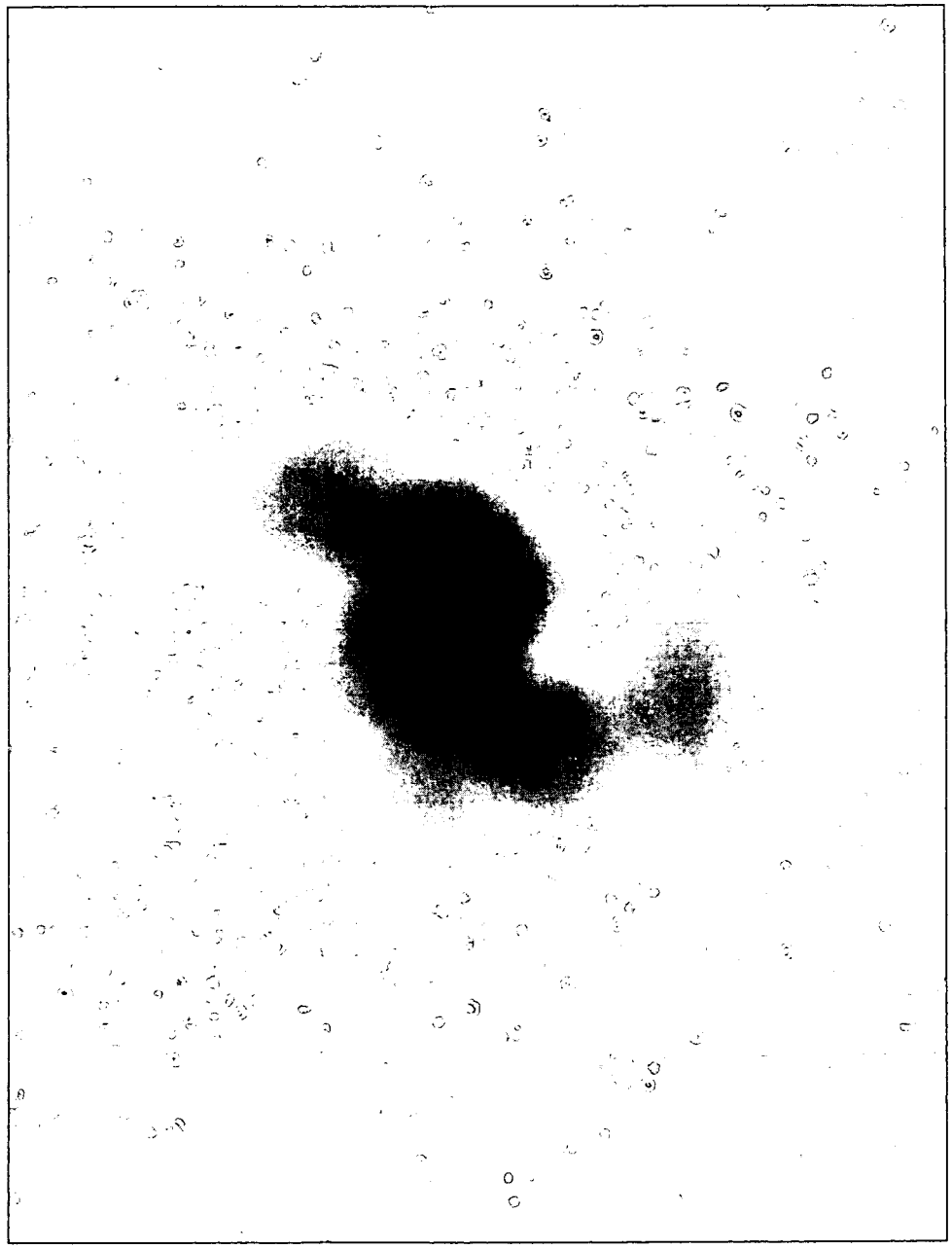
FIG. 7 is an image of a CFU-GEMM colony at Day 14 following culture of 20,000 nonadherent SVF cells (100× magnification).

While all three types of colonies, including BFU-E, CFU-GM and CFU-GEMM, were observed in each of the three cell populations assayed, the highest frequency being observed in the "nonadherent SVF" population. FIGS. 4-7 show representative colonies observed in nonadherent SVF cells. FIGS. 4 and 5 show BFU-E colonies at 40× magnification. FIG. 6 shows a CFU-GM colony and FIG. 7 shows a CFU-GEMM colony.

TABLE 1

|  | APWP | SVF | Nonadherent SVF |
| --- | --- | --- | --- |
| BFU-E | 1:25,000 | 1:2,000 | 1:600 |
| CFU-GM | None observed | 1:7,000 | 1:5,000 |
| CFU-GEMM | None observed | 1:50,000 | 1:25,000 |

Note:
APWP = aspirate post-wash pellet; BFU-E = burst forming unit-erythroid; GM = granulocyte, macrophage; GEMM = granulocyte, erythroid, macrophage, megakaryocyte The expression of aldehyde dehydrogenase (ALDH) has also been used to identify hematopoietic subpopulations. ALDH activity and PCR array analysis were performed to identify potential hematopoietic subpopulations within the nonadherent population of stromal vascular fraction of liposuction aspirates. Preliminary data indicated that the ALDH-$^{br}$SSC$^{lo}$ population comprises about 17% of the nonadherent SVF cell population.

Example 2

Bone Marrow Repopulation Assay Using Adipose-Derived HSCs

Human adipose tissue-derived hematopoietic stem cells obtained in Example 1 are tested for hematopoietic differentiation based on a bone marrow repopulation assay. Immunodeficient SCID or nude/beige mice are lethally-irradiated with 11 Gy of γ-irradiation in a split dose and maintained on a diet of acidified water and autoclaved food. Hematopoietic cells are isolated at quantities of approximately $10^7$ cells per transplant hematopoietic cells when of murine origin ($10^7$ bone marrow-derived cells) or approximately $10^6$ cells per transplant when of human origin ($10^6$ adipose-derived HSCs or $10^6$ SVF cells) and are introduced into the mice 16 hours following the lethal irradiation by injection through the tail vein or retro-orbital vein or intraperitoneally. Alternatively, the human cells are mixed with the murine hematopoietic cells at a ratio of approximately 1:10 prior to transplantation into a sub-lethally-irradiated host animal to assay competitive repopulation. Animals are transfused under methoxyflurane anesthesia.

Six to twelve weeks following transplantation, blood is collected from the recipient animals and subjected to flow cytometric analysis with specific monoclonal antibodies for human hematopoietic cell markers including, but not limited to, Thy 1 (T cell marker), B220 (B cell marker), Mac 1 (macrophage marker), and HLA (H-2K, human marker). The percentage of total peripheral hematopoietic cells of human versus murine origin is determined. In similar studies, bone marrow and spleen from recipient mice are harvested and subjected to in vitro clonogenic assays for specific hematopoietic lineages. These studies utilize methylcellulose colony based assays. Cells are analyzed using comparable immunofluorescent methods for specific lineage commitment.

Example 3

Bone Marrow Repopulation Assay Using Adipose-Derived HSCs

Human adipose tissue from an individual human donor is isolated by liposuction and adipose-derived HSCs are isolated in vitro according to the methods described above. The cells are cultured as primary cultures for a period of up to about 5 days following initial plating in Iscove's media containing 10% fetal bovine serum, 5% chick embryo extract, stem cell factor, flt-3 ligand and antibiotics at 37° C.

Cells are used immediately for patients with hematopoietic disorders, such as that following high dose chemotherapy, or cryopreserved for future use in the event of an acute medical need by the donor or a histocompatible recipient. Adipose-derived HSCs are infused into the recipient, whether as an autologous or allogeneic transplantation, following any event, such as chemotherapy or irradiation, that severely compromises bone marrow function and immune competence. Adipose-derived HSCs are marked with a fluorescent label to allow the physician to follow their fate following transplantation. Evidence of accelerated bone marrow recovery is monitored based on detection of newly synthesized hematopoietic cells (lymphoid cells, myeloid cells, erythroid cells, and platelets) in the peripheral blood stream based on flow cytometric methods.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for isolating a CD34$^+$ cell, the method comprising:
   obtaining adipose tissue,
   preparing a stromal vascular fraction (SVF) from the adipose tissue;
   incubating SVF cells in a stromal cell media in a cell culture apparatus for a time suitable for the culture of cells in vitro to allow the cells to adhere to the culture apparatus; separating nonadherent cells in the SVF from adherent cells in the SVF; and
   identifying CD34+ cells in the non-adherent cell population, and isolating the CD34$^+$ cells from the CD34− nonadherent cells,
wherein at least about 40% of the non-adherent cells are CD34$^+$ cells.

2. The method of claim 1, wherein the CD34$^+$ cell is isolated in the ratio of at least about 1×10$^7$ CD34$^+$ cells isolated per about 100 ml of adipose tissue.

3. The method of claim 1, wherein the obtaining step comprises lipoaspiration.

4. The method of claim 1, wherein the adipose tissue is human.

5. The method of claim 1, wherein the CD34$^+$ cell is selected from the group consisting of a CD34$^+$SSC$^{lo}$ cell, a CD34$^+$ CD45$^+$ cell, a CD34$^{hi}$CD38$^-$CD4$^-$cell, a CD34$^+$ $CD38^- CD41^- SSC^{lo}$, a $CD34^{lo}CD45^-$ cell, a $CD34^{lo}CD45^+$ cell, a $CD34^+ ALDH^{br}$ cell and a $CD34^+ ALDH^{br} SSC^{lo}$ cell.

6. The method of claim 1, further comprising the step of isolating a $CD34^{hi}$ cell or a $CD34^{lo}$ cell.

7. The method of claim 1, wherein the $CD34^+$ cell is selected from the group consisting a colony-forming unit granulocyte macrophage (CFU-GM), a burst-forming unit erythrocyte (BFU-E) and a colony-forming unit granulocyte erythrocyte macrophage megakaryocyte (CFU-GEMM).

8. The method of claim 1, further comprising harvesting the adherent cells, thereby harvesting adipose tissue-derived stromal cells.

* * * * *